United States Patent
Wright et al.

(10) Patent No.: US 10,172,743 B2
(45) Date of Patent: Jan. 8, 2019

(54) COMPRESSION ELEMENT

(71) Applicant: PROVENSIS LIMITED, London, Greater London (GB)

(72) Inventors: David Dakin Iorwerth Wright, London (GB); Stephen Tristram, Basingstoke (GB)

(73) Assignee: Provensis Limited, London (GB)

( * ) Notice: Subject to any disclaimer, the term of this patent is extended or adjusted under 35 U.S.C. 154(b) by 435 days.

(21) Appl. No.: 14/211,911

(22) Filed: Mar. 14, 2014

(65) Prior Publication Data

US 2014/0309567 A1    Oct. 16, 2014

Related U.S. Application Data

(60) Provisional application No. 61/787,713, filed on Mar. 15, 2013.

(51) Int. Cl.
*A61H 9/00* (2006.01)
*A61B 17/132* (2006.01)
(Continued)

(52) U.S. Cl.
CPC .......... *A61F 13/06* (2013.01); *A61B 17/1325* (2013.01); *A61H 9/005* (2013.01); *A61B 8/0891* (2013.01)

(58) Field of Classification Search
CPC .. A61F 13/06; A61F 13/08; A61F 5/30; A61F 5/32; A61F 13/00029;
(Continued)

(56) References Cited

U.S. PATENT DOCUMENTS

| | | | | |
|---|---|---|---|---|
| 3,294,387 A | * | 12/1966 | Chavannes | B29C 66/45 267/145 |
| 3,306,288 A | * | 2/1967 | Rosenfield | A61F 13/061 450/156 |

(Continued)

FOREIGN PATENT DOCUMENTS

| | | |
|---|---|---|
| DE | 2808527 | 9/1979 |
| EP | 2532327 | 11/2006 |

(Continued)

OTHER PUBLICATIONS

Ferrara, Francesco et al., "Sclerotherapy in the patient with diabetes: indications and results", Phlebolymphology, vol. 19.2012, 2012, 193-198.

(Continued)

*Primary Examiner* — Colin W Stuart
*Assistant Examiner* — Douglas Sul
(74) *Attorney, Agent, or Firm* — Finnegan, Henderson, Farbow, Garrett & Dunner, L.L.P.

(57) ABSTRACT

A venous compression element is provided which is useful in the treatment of chronic venous insufficiency, such as varicose veins. The compression element comprises a central core of fluid filled cells and an outer layer of soft material suitable for maintaining contact with skin for a prolonged period of time and which covers the core. A particular embodiment comprises a folded or rolled cylindrical core of air or nitrogen filled bubble wrap sheet material covered by a skin compatible bandaging material. The compression elements described are particularly useful in providing consistent compression to a blood vessel after endovenous endothelial wall damaging techniques.

16 Claims, 2 Drawing Sheets

Figure 1A:
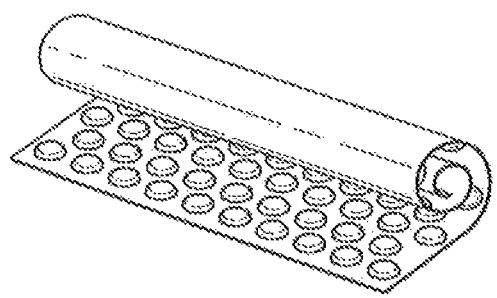

(51) Int. Cl.
*A61F 13/06* (2006.01)
*A61B 8/08* (2006.01)

(58) Field of Classification Search
CPC ............... A61F 13/085; A61F 13/102; A61F 2013/0028; A61B 8/0891; A61B 17/00; A61B 17/12; A61B 17/132; A61B 17/1322; A61B 17/135; A61H 9/0092; A61H 9/0078; A61H 2201/164; A61H 2201/1695; A61L 38/0891
USPC ......... 602/13, 60–63, 75, 79; 606/201–203; 206/522; 383/3
See application file for complete search history.

(56) References Cited

U.S. PATENT DOCUMENTS

| | | | | |
|---|---|---|---|---|
| 3,826,249 | A | | 7/1974 | Lee et al. |
| 4,243,028 | A | * | 1/1981 | Puyana ............... A61F 13/108 602/62 |
| 4,730,610 | A | * | 3/1988 | Graebe ............... A61F 13/069 128/882 |
| 5,063,913 | A | * | 11/1991 | Nyi ................... A61F 13/107 602/20 |
| 5,156,629 | A | * | 10/1992 | Shane ................. A61F 2/7843 128/DIG. 20 |
| 5,366,439 | A | * | 11/1994 | Peters ................. A61F 5/0127 602/13 |
| 5,419,757 | A | * | 5/1995 | Daneshvar ............ A61F 5/012 128/DIG. 20 |
| 5,681,203 | A | * | 10/1997 | Arnold ................ A63H 5/00 242/598 |
| 6,336,907 | B1 | * | 1/2002 | Dono .................. A47C 7/467 601/148 |
| 6,592,534 | B1 | * | 7/2003 | Rutt ................... A61H 9/0078 601/151 |
| 7,135,007 | B2 | * | 11/2006 | Scott .................. A61F 13/085 602/75 |
| 2008/0312570 | A1 | * | 12/2008 | Dunagan .............. A61F 13/046 602/3 |
| 2009/0062703 | A1 | | 3/2009 | Meyer et al. |
| 2014/0163606 | A1 | | 6/2014 | Ragg |

FOREIGN PATENT DOCUMENTS

| | | |
|---|---|---|
| FR | 2885295 | 12/2008 |
| WO | WO-2006/053920 | 0/2006 |

OTHER PUBLICATIONS

English language Derwent Abstract for DE-2808527.
English language Derwent Abstract for FR-2885295.

\* cited by examiner

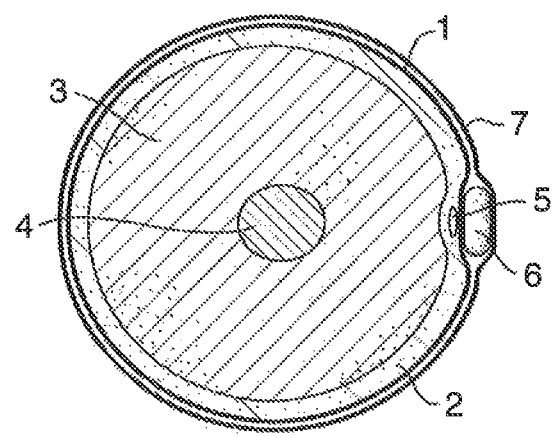
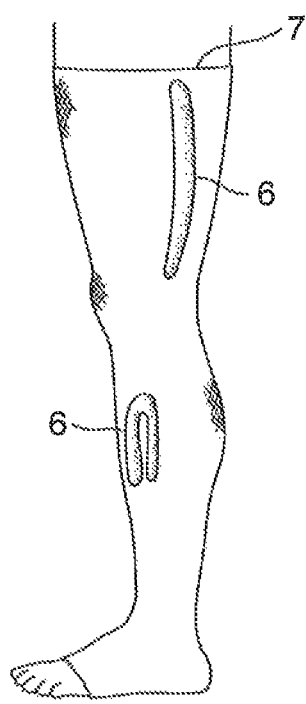
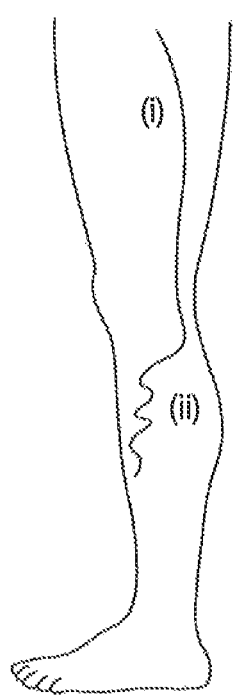

COMPRESSION ELEMENT

The present invention relates to a compression element for use in treatment of venous disease, such as varicose veins and similar disorders requiring application of comfortable but firm pressure to a particular section of a human or animal limb, particularly an area of the upper or lower leg. In particular the element is in the form of a pad.

It is known to apply compression pads to a limb to treat chronic venous insufficiency directly or after endovenous treatment to eliminate varicose veins in order to aid in recovery and to reduce inflammation. This has previously been provided by foam rubber pads (Medi), or folded roll of aluminium foil covered in cotton wool (Bernbach) or compound material pads (Begnini). Problems with each of these earlier solutions include crushing, irregularity, heaviness and inflexibility of the pads.

WO2006053920 (Cabrera) discloses a method of applying pressure to a selected region of a human limb, after treatment of varicose veins by sclerotherapy or other endoluminal techniques, in order to provide reduction of the inflammatory response of the vessels, as well as to reduce the time it takes for their disappearance. The most striking results are said to be provided in the larger diameter vessels.

The Cabrera method employs an inelastic inextensible support, adjustable to the shape of the limb. The support includes a linear pressure element on its inner surface, which incorporates a pneumatic or hydraulic chamber, with a corresponding inlet for cooperating with an input device equipped with a manometer for controlling with precision pressure applied to a piston element and, consequently, the localized area of the patient's limb. Particularly this method applies a selective pressure that is localised to the vessel or vessels that have been treated, such that the pressure does not affect healthy blood vessels and, consequently, does not affect the normal venous return of the limb in question.

This device is preferably such that the localized pressure is adjustable, in order to be able to apply only sufficient pressure to ensure that the treated vessels remain empty of blood, while the process of healing and fibrosis of the vein as a result of the endovenous treatment completes.

WO2012/001410 (Barker) discloses a compression stocking for applying pressure to inter alia varicose veins, sports fatigue and similar conditions. Particularly it describes a graduated compression stocking for pushing blood into the deep vein system and thus enhancing that flow by using a panel in the stocking to enable targeted compression of one or more particular sites. One embodiment of this panel has a number of rounded protrusions of progressively smaller diameter. These protrusions are built up from plastics material positioned at predetermined lower, middle or upper parts of a stocking.

The present applicant has sought to improve the operation of a compression element, for use in treating a human or animal limb, such that it retains an even pressure along its entire extent, in a simple and reliable manner.

In the applicant's element, a simplified structure is provided that is manufacturable from simple staple cellular materials whilst being robust enough to perform its task for the weeks that it must be applied to a patient limb. This invention further seeks to avoid the problem associated with the continuous gas filled pouch whereby the gas moves from higher pressure areas to the lower ones distorting the compression effect. Any liquid filled tube has a similar problem. The advantages are that the element is effectively incompressible at clinical pressure, of very low weight thus making it easy to wear over a number of days or weeks, it is soft and flexible, and can be cut to length, with a low cost of materials. Use of the invention alleviates skin contact problems such as allergic, sweat related contact issues that can be associated with prior art devices.

In a first aspect the present invention provides a venous compression element comprising a central core of fluid filled cells and an outer layer of soft material suitable for maintaining contact with skin for a prolonged period of time covering the core.

In a second aspect the present invention provides a compression element for use in the treatment of varicose veins after endovenous endothelial wall damaging techniques comprising a central core of fluid filled cells and an outer layer of soft material suitable for maintaining contact with skin for a prolonged period of time covering the core.

The compression element is suitable for use in the treatment of venous insufficiency, such as varicose veins, to provide even and continuous compression as part of traditional compression therapy. The compression element is suitable for use in the treatment of varicose veins after endovenous endothethial wall damaging techniques. Such techniques are well known and include sclerotherapy and other ablation therapies.

The fluid filled cells of the central core may be filled with liquid or gas. In a particular embodiment, the core comprises gas filled cells, such as nitrogen or air filled cells, although it will be understood that virtually any gas will be suitable, provided it is non-corrosive to the material from which the cells are formed. In a particular embodiment, the core comprises a plastics laminate material formed such as to encapsulate discrete air filled cells between two or more layers of plastics sheet. Polymer laminate materials are well known in the art and essentially any polymer which is capable of forming a plurality of discrete fluid filled cells will be suitable, provided that the polymer is essentially impermeable to the fluid which fills the cells. Examples of such sheet material encapsulating gas filled cells have been available for over 40 years and are described in prior art U.S. Pat. No. 3,142,599, U.S. Pat. No. 5,665,456 and application US2009/0017261

Particularly advantageously, the core is arranged as a cylindrically formed contiguous body of gas filled plastics cells, and particularly comprises regularly spaced, protruding hemispheres of fixed volume and, more advantageously, being a sheet of cellular bubble encapsulating material, such as that known as 'bubble wrap', folded or rolled into a cylinder and covered with tubular bandage. The sheet may be of any convenient length, but typically would be a rectangle with sides of between 20 and 50 cms length. This is conveniently folded or rolled upon itself with a bubble projection surface facing inward and a flat base layer facing outward. The cylinder so formed should preferably be of 10 to 50 mm diameter, more preferably of 20 to 40 mm diameter and most preferably of 25 to 30 mm diameter.

The cylinder of folded or rolled foam is conveniently covered with a tubular bandage such as Molnlycke Tubinette, eg size 12 or similar, with a number of such tubular bandages being applied in preferred embodiments, for example 2, 3 or 4 one upon the other.

The sheet material encapsulating fluid filled cells is conveniently a bubble wrap such as that provided by Sealed Air Corporation, New Jersey USA under the brand AirCap. Preferred is a cell diameter (as measured on the base layer) of between 6 and 14 mm, particularly about 9 to 11 mm and conveniently an AirCap material with 9.5 mm diameter cells is preferred. AirCap material is double layered plastics which provides improved resistance to loss of gas pressure. Aircap and Tubinette are trademarks of Sealed Air Corporation and Molnlcke respectively.

Use of such folded or rolled sheet material having gas fluid filled cells, particularly double skinned such as AirCap, renders the compression element effectively incompressible at physiological pressure, with essentially complete resistance to crushing at 0-50 mm/Hg (0 to 0.05 atmospheres) for a one to two week interval over which it is applied to a patient.

These characteristics allow the compression element of the invention to be applied to a limb over the site of a pre-treated vein and held in place with windings of bandages or a compression stocking to provide the inward directed force.

In use the compression element of the invention is applied to a skin surface and oriented with its major dimension (length) aligned with a blood vessel that has been treated, eg. by sclerotherapy, laser ablation or radiofrequency ablation treatment. Conveniently, the compression element will be of a preformed length such that a predetermined length of blood vessel, or the entire blood vessel, is compressed. In a particular embodiment, two or more compression elements are aligned to provide constant compression along the length of the great saphenous vein (GSV). In this embodiment, individual compression elements, aligned with the GSV, are placed above and below the patient's knee to provide continuous compression to a treated GSV without restricting movement of the knee joint. After placement of the compression element, a compression bandage or stocking is applied to the skin, e.g. such as a surgical stocking applied when the skin is on a leg that has been treated for varicose veins, whereby the bandage or stocking holds the compression element in place. This maintains the treated vessel, eg. a vein, empty such as to facilitate healing a fibrosis in the days after the treatment.

Consequently, in a further aspect, the invention provides a method of treatment of varicose veins comprising applying to a skin surface a compression element as described herein and orienting the compression element with its major dimension (length) aligned with a blood vessel that has been treated, eg. by sclerotherapy, laser ablation or radiofrequency ablation treatment.

The present invention will now be further illustrated by reference to the following non-limiting figures and examples below. Further embodiments of the invention will occur to those skilled in the art in the light of these.

FIGURES

FIGS. 1a-d: show steps in converting a sheet of Aircap material into a compression element of the invention as described in Example 1 below.

FIGS. 2a-c: show application of the compression element to the surface of a leg after the treatment of a varicose vein therein using a stocking or bandage as described in Example 3.

EXAMPLE 1. COMPRESSION ELEMENT

A compression element according to the present invention is assembled as shown in FIGS. 1a, 1b, 1c and 1d of FIG. 1.

A sheet of Aircap bubble wrap of 9.5 mm cell diameter is cut to a rectangle 37 cm by 30 cm and rolled upon itself about its longer side to produce a cylindrical tubular central core. This inner core is placed within a single Molnlycke Tubinette size 12 bandage using a Tubinette applicator and the ends twisted to enclose it in place within a surface suitable for prolonged contact with skin. Excess length of bandage is folded back over one or both ends of the covered tubular core.

Figure 1B:
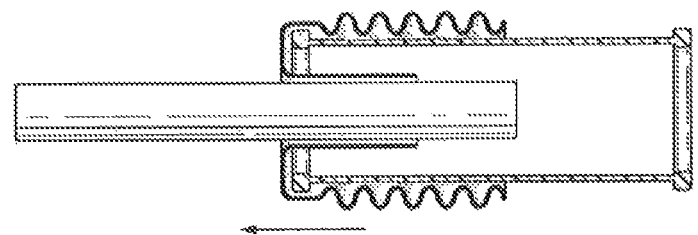
Figure 1C:
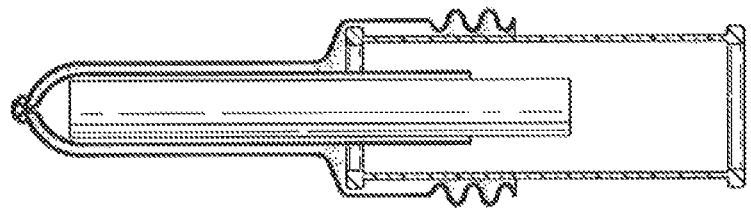
Figure 1D:
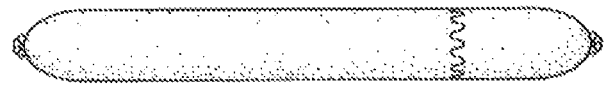

FIG. 1a shows a sheet of Aircap 'bubble wrap' rolled upon itself; FIG. 1b shows insertion of the rolled sheet into a Tubinette size 12 bandage using a Tubinette applicator (Molnlycke); FIG. 1c shows closure of the distal end by twisting of the bandage end according to manufacturers instructions and FIG. 1d the closure of the proximal end by twisting and folding back on itself of any excess bandage length.

EXAMPLE 2. TREATMENT PROCEDURE WITH MICROFOAM

Use of the Polidocanol Endovenous Microfoam (PEM) is administered under duplex ultrasound guidance, the incompetent GSV and/or incompetent accessory saphenous veins (veins to be treated), all perforators and distal varicosities, and the point for cannulation were to be marked with the patient in a standing position after the patient stood for 10 minutes. The recommended point for cannulation was a straight segment of vein in the lower mid-thigh for the GSV or slightly higher for accessory saphenous veins. Once the veins were marked, the patient was laid on his or her back and the vein to be treated was cannulated using ultrasound guidance. A manometer tube previously filled with sterile heparinized normal saline solution was connected to the cannula and venous access confirmed by checking both the dark colour and low pressure of blood aspirated from the vein. The leg was then elevated above the central circulation. Treatment commenced by connection of a syringe of freshly generated study product to the manometer tubing and injection of the study product into the cannulated vein. Treatment proceeded from proximal to distal veins.

Initial Injection of the Great or Accessory Saphenous Vein

1. A syringe of freshly-generated PEM was connected to the manometer tube in preparation for the initial injection to fill the GSV to the SFJ. The initial injection was to be no more than 5 mL (plus the 2 mL allowed for dead space).
1. The vein to be treated was occluded distal to the cannula using finger pressure and the microfoam was injected slowly (approximate rate of injection 1 mL/second in the GSV and 0.5 mL/second in smaller accessory veins) to fill the proximal GSV.
2. With ultrasound in longitudinal view, the SFJ was constantly monitored. Injection was stopped as soon as microfoam was seen arriving 3-5 centimeters (cm) distal to the SFJ and distal to the junction with the superficial epigastric vein.
3. The longitudinal view of the microfoam column within the vein was maintained, and digital pressure over the terminal segment of the GSV sufficient to stop the column of microfoam from moving was applied. Simultaneously, finger compression distal to the cannulation site was removed. It was confirmed that the femoral vein remained patent. Special care was employed if a perforator vein was present, to minimize the risk of microfoam entering the deep venous system.
4. After 1 minute of proximal digital compression, the ultrasound probe was moved to interrogate other areas of the vein until venospasm fully developed.

5. Efficacy of the procedure was determined by ultrasound observation of venospasm of the treated vein as evidenced by a very constricted lumen (<1 mm) that was filled with microfoam. As seen on ultrasound, the vein was much reduced in diameter or completely collapsed, and in longitudinal section appeared as a fine white line. As the proximal digital compression was released, any movement of the microfoam column in the vein was observed. If it was slow or stationary, the pressure could be removed completely; if movement of the microfoam was more rapid, pressure was reapplied for a further period of time (2-3 minutes).

6. If, following the first injection, venospasm was not observed within 5 minutes, a further injection of 4-6 mL could be given in the same manner. When venospasm of the proximal segment was confirmed on ultrasound, the distal GSV injection procedure could be followed.

Injection of Distal Varicosities

The instructions that follow were to be used only if cannulation was successful through 1 puncture site. If the vein was punctured 2 or more times, distal filling via the cannulation site should not be attempted.

A clear duplex image of the targeted distal varicosities was to be established.

7. Using the same cannulation site, the new syringe of freshly generated microfoam was attached to the in situ cannula via the manometer tube.

8. The treated vein was occluded with finger pressure just proximal to the tip of the cannula and microfoam was injected slowly at a rate of approximately 0.5 mL per second.

9. The filling was observed by duplex scanning, and care was to be taken to avoid uncontrolled microfoam passing through pre-marked perforators. Forced dorsiflexion of the foot was to be applied to close the perforators as soon as microfoam was known to have passed the knee and was to be continued until venospasm was seen in the treated veins, or up to 5 minutes. Digital compression should be applied over the marked perforating veins as microfoam is seen to arrive close to the junction between the superficial vein and the perforator.

Injection was to be stopped when all the distal varicose veins to be treated were filled with microfoam. The distal varicosities were to be monitored by duplex imaging to confirm venospasm. If residual varicosities (greater than 3 mm in diameter) that had not been filled with microfoam were evident, further local injections could be undertaken with a butterfly needle to complete treatment, up to a maximum total volume administered per treatment session of 15 mL.

If a butterfly needle could not be inserted with the leg in the elevated position, the leg was NOT to be lowered, because when injecting distal varicosities, the risk of microfoam entering the perforating veins is increased. Dorsiflexion of the foot was to be applied (as above) to limit spread of microfoam to the deep veins.

EXAMPLE 3: APPLICATION OF COMPRESSION ELEMENT OF THE INVENTION

FIG. 2a shows a cross section of a leg, with skin (1), subcutaneous tissue (2), muscle (3), femur (4) and with a varicose vein (5) having the compression element (6) held in place at the nearest surface of the skin using a stocking or wrapped bandage (7). FIG. 2b shows two possible orientations of the element (6) on a sclerosed varicose vein (5) the location of which is illustrated in FIG. 2c. The element (6) can be applied, (i) in elongate form lying along the surface of the skin about an elongate stretch of treated vein (i) or folded above an area of reticulation (ii).

Post-Procedure Compression Care

Patients were to be fitted with bandaging and a compression stocking as soon as the treatment was complete.

10. Compression should be applied to the treated leg before it is lowered. A limited stretch bandage is applied to the leg, working from the ankle upwards. Application was paused at the groin.

11. Compression pads of the invention—as described in Example 1—are applied on top of the stretch bandage along the course of the GSV (or other treated accessory saphenous vein) and over prominent superficial varicosities that had been treated.

12. Application of limited stretch bandage is then continued from the groin back to the ankle. This second layer of stretch bandage holds the compression pads in place.

13. A thin overstocking is fitted.

14. Finally, a Class II (i.e., 30-40 millimeters of mercury [mmHg]) compression thigh-length stocking with hip extension was fitted.

15. The patient is then mobilized and encouraged to walk for 10 minutes.

16. Patients were required to walk for 5 minutes during each waking hour for the first 14 days after treatment.

The compression bandages and stocking are worn continuously for the first 48 hours following treatment. Thereafter, the Class II compression stocking is to be worn alone for a further 12 days, for a total of 14 days of compression, 24 hours a day, to the treated leg following the procedure.

The invention claimed is:

1. A venous compression element comprising:
   at least one central core element formed of laminate material encapsulating a plurality of discrete fluid filled cells between two or more layers of the laminate material cylindrically folded or rolled upon itself and covered with one or more tubular bandages so that the central core element is in contact with at least one of the tubular bandages, wherein an outer portion of the one or more tubular bandages is configured to be placed at discrete locations against a patient's skin to provide compression; and
   an outer layer of soft material suitable for maintaining contact with skin for a prolonged period of time covering the at least one core element.

2. A venous compression element as claimed in claim 1 wherein the core comprises gas filled cells.

3. A venous compression element as claimed in claim 2 wherein the gas is air or nitrogen.

4. A venous compression element as claimed in claim 1 in that the core is arranged as a cylindrically formed contiguous body of air filled plastics cells.

5. A venous compression element as claimed in claim 1 wherein the core is a sheet of cellular bubble encapsulating material, comprising regularly spaced, protruding hemispheres with a fixed amount of fluid.

6. A venous compression element as claimed in claim 5 wherein the sheet is a rectangle of between 20 and 50 cms length.

7. A venous compression element as claimed in claim 5 wherein the sheet is folded or rolled upon itself with a bubble projection surface facing radially inward and a flat base layer facing radially outward.

8. A venous compression element as claimed in claim 5 wherein the cylinder so formed is of 10 to 50 mm diameter.

9. A venous compression element as claimed in claim 8 wherein the cylinder is of 20 to 40 mm diameter.

10. A venous compression element as claimed in claim 1 wherein the laminate material encapsulating fluid filled cells is a bubble wrap sheet material comprising a bubble projection surface and a base layer.

11. A venous compression element as claimed in claim 10 wherein the sheet material has a cell diameter, as measured on the base layer, of between 6 and 14 mm.

12. A venous compression element as claimed in claim 10 wherein the sheet material has a cell diameter of from 9 to 11 mm.

13. A venous compression element as claimed in claim 12 wherein the sheet is a double layered plastics which provides improved resistance to loss of gas pressure.

14. A venous compression element as claimed in claim 1 adapted to treat varicose veins in a patient in need thereof, wherein the compression element is configured to be applied to the skin surface and aligned with a vein after performance of an endovenous endothethial wall damaging technique.

15. A venous compression element as claimed in claim 1 wherein the compression element is adapted to provide essentially complete resistance to crushing at 0-50 mm/Hg and 0 to 0.1 atmospheres for a one to two week interval over which it is applied to a patient.

16. A venous compression element as claimed in claim 1 wherein the compression element is in the form of a compression pad.

* * * * *